United States Patent [19]

Takano et al.

[11] 4,347,396

[45] Aug. 31, 1982

[54] PROCESS FOR PRODUCING STYRENE

[75] Inventors: Hirotaka Takano; Hideyuki Takahashi; Ryoichi Hirogohri; Kohji Kato, all of Yokkaichi, Japan

[73] Assignee: Mitsubishi Petrochemical Co., Ltd., Tokyo, Japan

[21] Appl. No.: 246,012

[22] Filed: Mar. 20, 1981

[30] Foreign Application Priority Data

Mar. 27, 1980 [JP] Japan ................................ 55-39196

[51] Int. Cl.$^3$ ............................................. C07C 15/10
[52] U.S. Cl. ..................................................... 585/441
[58] Field of Search ........................................ 585/441

[56] References Cited

U.S. PATENT DOCUMENTS

| | | | |
|---|---|---|---|
| 2,331,427 | 10/1943 | Schulze et al. | 585/441 X |
| 2,509,900 | 5/1950 | Wormith | 585/441 |
| 2,851,502 | 9/1958 | Bowman et al. | 585/441 X |
| 3,118,006 | 1/1964 | Lovett et al. | 585/441 |
| 3,502,737 | 3/1970 | Ghublikian | 585/441 |
| 3,660,510 | 5/1972 | Kindler et al. | 585/441 X |
| 3,751,232 | 8/1973 | Borre et al. | 585/441 X |
| 3,755,482 | 8/1973 | Munnally et al. | 585/441 |
| 3,830,864 | 8/1974 | Borre et al. | 585/441 |
| 3,868,428 | 2/1975 | Cox | 585/441 |

*Primary Examiner*—Paul F. Shaver
*Attorney, Agent, or Firm*—Oblon, Fisher, Spivak, McClelland & Maier

[57] ABSTRACT

A process for producing styrene by dehydrogenation of ethylbenzene comprising feeding steam and ethylbenzene to three or more dehydrogenation reactors connected in series, an intermediate heater for heating the reaction mixture through heat exchange with steam being provided between each of said dehydrogenation reactors, said steam being first used as a medium to heat the respective intermediate heaters, and then mixed with ethylbenzene supplied as the feed to the first of said series of reactors, wherein 3 to 10 mols of steam are mixed with one mol of ethylbenzene and the temperature and pressure at the inlet of the final dehydrogenation reactor are 600°–680° C. and 0.4–0.8 Kg/cm$^2$ (abs.), respectively, is disclosed.

4 Claims, 1 Drawing Figure

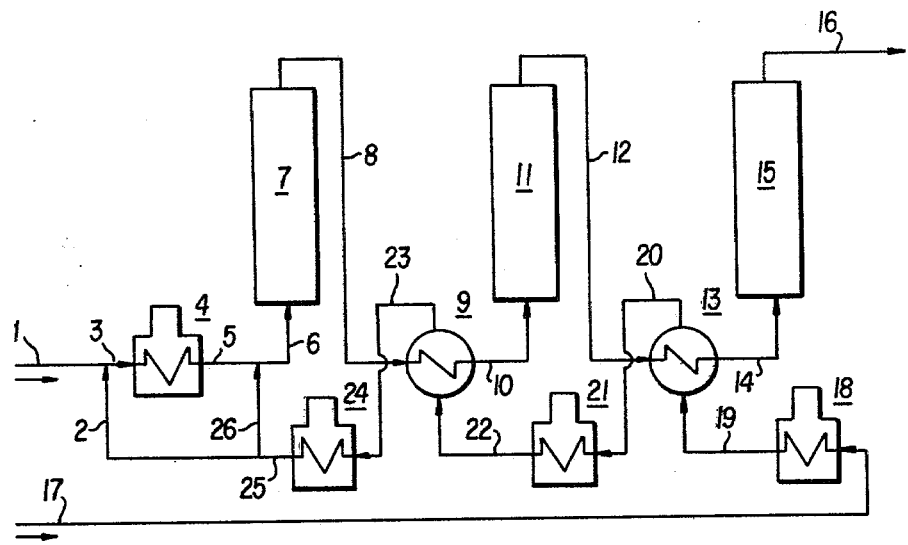

PROCESS FOR PRODUCING STYRENE

BACKGROUND OF THE INVENTION

1. Field of the Invention

This invention relates to a process for producing styrene by dehydrogenation of ethylbenzene.

2. Description of the Prior Art

It is known to produce styrene by dehydrogenating ethylbenzene using an iron-based dehydrogenating catalyst, ethylbenzene being diluted with a large amount of steam. The steam used as the diluent has several other functions, e.g., it supplies the heat necessary for dehydrogenation, reduces the partial pressure of the reactants, and decokes the carbon on the catalyst by reaction with an aqueous gas. It is difficult to recover the heat not used in the reaction from the steam and a huge amount of heat is left unrecovered when steam is used in large volume. The reduction of the amount of steam used in the dehydrogenation of ethylbenzene is a greatly desired benefit to process economy and several attempts have been made to achieve this end. A typical example is a reactor of the external heating type. This reactor reduces the amount of steam by supplying the required amount of heat from outside of the reaction pipes, but, because of the use of shell—and—tube pipes to heat the catalyst bed from the outside, a large—scale reactor cannot be installed, and the construction cost is higher than that of the common downflow reactor or radial flow reactor.

Efficient production of styrene by dehydrogenation of ethylbenzene depends on the conversion of ethylbenzene and the selectivity of converted ethylbenzene for styrene, and the higher these parameters, the less steam used. Steam used in the dehydrogenation of ethylbenzene has the following function: (1) it affects the equilibrium conversion of ethylbenzene, i.e. it shifts the equilibrium by reducing the partial pressure of the reactants, and the more steam that is used, the greater the equilibrium conversion of ethylbenzene; (2) it prevents coking during the dehydrogenation; and (3) it supplies the heat required for dehydrogenation. For these reasons, 13 to 16 mols of steam per mol of ethylbenzene are conventionally necessary to produce styrene by dehydrogenation of ethylbenzene, and the conversion of ethylbenzene achieved is only about 60%, and 70% at most. Hence, in the conventional method, a great deal of unreacted ethylbenzene must be recirculated and this results in a corresponding increase in the amount of steam required.

A need therefor continues to exist for a process for the production of styrene by the dehydrogenation of ethylbenzene wherein the energy cost, i.e. the steam requirements, are greatly reduced.

SUMMARY OF THE INVENTION

Accordingly, one object of this invention is to provide a process for the production of styrene by the dehydrogenation of ethylbenzene.

Another object of this invention is to provide a process for the production of styrene from ethylbenzene with reduced steam requirements.

Briefly, these objects and other objects of the invention as hereinafter will become more readily apparent can be attained by providing a process for producing styrene by dehydrogenation of ethylbenzene comprising feeding steam and ethylbenzene to three or more dehydrogenation reactors connected in series, an intermediate heater for heating the reaction mixture through heat exchange with steam being provided between each of said dehydrogenation reactors, said steam being first used as a medium to heat the respective intermediate heaters, and then mixed with ethylbenzene and supplied as the feed to the first of said series of reactors, wherein 3 to 10 mols of steam are mixed with one mol of ethylbenzene and the temperature and pressure at the inlet of the final dehydrogenation reactor are 600°–680° C. and 0.4–0.8 kg/cm$^2$ (abs.), respectively.

In a preferred embodiment of the invention, the temperature and pressure at the inlet of the dehydrogenation reactors, other than that of the final stage, are 600°–680° C. and 2 to 0.4 kg/cm$^2$ (abs.), respectively.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawing, wherein:

The FIGURE is a representation of an embodiment of the process using three dehydrogenation reactors connected in series.

DETAILED DESCRIPTION OF THE PREFERRED EMBODIMENTS

This invention is based on studies directed to reducing the amount of steam used in the dehydrogenation of ethylbenzene to produce styrene. It was found that the desorption of styrene from the dehydrogenation catalyst has a significant effect on the efficiency of the reaction and that under high temperature and low pressure, styrene is easily desorbed, coking seldom takes place on the catalyst, and the conversion of ethylbenzene is increased, thus, reducing markedly the amount of steam necessary for achieving increased conversion. It was found that under these conditions, a reaction product of increased styrene content can be obtained by using less than 10 mols of steam per mol of ethylbenzene, without adversely affecting the performance of the catalyst. Therefore, this invention provides a novel process for producing styrene by dehydrogenation of ethylbenzene wherein three or more dehydrogenation reactors connected in series are used, an intermediate heater for heating the reaction mixture through heat exchange with steam is provided between each of said dehydrogenation reactors, said steam being first used as a medium to heat the respective intermediate heaters and then mixed with ethylbenzene and supplied as the feed to the first of said series of reactors, wherein 3 to 10 mols of steam are mixed with one mol of ethylbenzene and the temperature and pressure at the inlet of the final dehydrogenation reactor are 600°–680° C. and 0.4–0.8 kg/cm$^2$ (abs.), respectively.

Preferably, the temperature and pressure at the inlet of the dehydrogenation reactors, other than that of the final reactor, are 600°–680° C. and 2 to 0.4 kg/cm$^2$ (abs.) respectively.

Since three or more reactor units, in series, are used in the process of this invention, only a small temperature drop of the reaction mixture occurs in each reactor unit. In addition, the reaction mixture is reheated in a heater between each of the reactors, allowing the temperature range effective for the reaction to be used fully. For these two reasons, an improved conversion of ethylbenzene can be achieved. Basically, the reaction system is placed under high temperature and low pressure conditions, so less steam is sufficient to achieve the desired reaction. Moreover, because additional required energy is supplied by heating between each reactor, less steam is required as a heat source for the reaction. Additionally, the reactor in the final stage which provides a reaction product of increased styrene content is operated at less than 0.8 kg/cm$^2$ (abs.) and adequate desorption of styrene from the surface of the catalyst is realized, and, in consequence, improved equilibrium conversion is obtained and high conversion and selectivity far beyond what has been accomplished conventionally are obtained to provide styrene in high yield. By way of example, in the conventional production of styrene by two-stage reaction, the conversion of ethylbenzene is only about 60% at a steam/ethylbenzene molar ratio of about 13, whereas in the process of this invention based on a three-stage reaction, an ethylbenzene conversion of 80% or more can be achieved at a steam/ethylbenzene molar ratio of 10 or less. The pressure drop is proportional to the number of reactors used and no appreciable advantage to the reaction results from using a larger number of reactors. Therefore, three reactors, connected in series, are preferably used in the practice of this invention.

Any type of reactor can be used in this invention for dehydrogenating ethylbenzene, and a radial flow reactor wherein pressure loss due to the catalyst bed is small is used with advantage because the pressure in the whole reaction system can be reduced to a level that matches the pressure in the final stage. There is also no particular limitation on the type of catalyst used in dehydrogenation of ethylbenzene. Generally, iron oxide based particulate catalysts containing chromium and potassium are used. Needless to say, a catalyst having highly selectivity is desired for making the most of the advantage of this invention.

One embodiment of the process of this invention wherein three units of dehydrogenating reactor are used is described hereunder by reference to the flowsheet represented in the accompanying FIGURE.

Ethylbenzene supplied through a line 1 is mixed with a small amount of steam through a line 2 for prevention of coking, and is then supplied through a line 3 to a heating oven 4 where it is heated preliminarily. The heated ethylbenzene 5 is mixed with steam through a line 26 and the mixture is directed into a first reactor 7 after the steam/ethylbenzene molar ratio ($H_2O$/EB) is adjusted to 10 or less, preferably, 3 to 8, and the temperature at the inlet of the reactor is adjusted to 600°–680° C., and the lowest possible pressure is used depending upon the pressure at the inlet of the reactor in the final stage and the pressure loss that develops in passing through the reactors, heat exchangers and piping on the line to the final reactor.

Preferably, the pressure at the inlet of the reactor is adjusted to 2–0.4 kg/cm$^2$ (abs.).

The temperature of the reactor mixture coming out of the first reactor 7 is several tens of degrees Celsius lower than that at the inlet of the reactor 7 because the reaction taking place in that reactor is endothermic, and then, the mixture is supplied through a line 8 to a heat exchanger 9 where it is heated again to the temperature at the inlet of the reactor 7, and supplied through a line 10 to a second reactor 11. The pressure at the inlet of the second reactor 11 is slightly lower than that at the inlet of the first reactor 7. The reaction mixture coming out of the second reactor is sent through a line 12 to a heat exchanger 13 where it is heated again and from which it is sent through a line 14 to the final reactor 15. The temperature at the inlet of the final reactor 15 is between 600° and 680° C. and is equal to or slightly higher than the temperature at the inlet of the other reactors. The pressure at the inlet of the final reactor is between 0.4 and 0.8 kg/cm$^2$ abs., preferably less than 0.7 kg/cm$^2$ abs. The reaction product out of the final reactor 15 is subsequently sent to a styrene refining step through line 16.

Steam is processed as follows in the system of this invention. Being supplied through a line 17, steam or pure water for providing steam is heated in a heating oven 18 to form superheated steam which is then supplied through a line 19 to the heat exchanger 13 where it heats the reaction mixture from the second reactor 11 to a temperature between 600° and 680° C. The steam whose temperature has been reduced as a result of heat exchange is supplied through a line 20 to a heating oven 21 where it is heated again and from which it is supplied through a line 22 to the heat exchanger 9 where it heats the reaction mixture from the first reactor. The steam out of the heat exchanger 9 is supplied through a line 23 to a heating oven 24 where it is heated to the temperature required for it to become suitable for mixing with ethylbenzene supplied through the line 1. As described before, a small part of the superheated steam from the heating oven 24 is passed through the line 2 and mixed with ethylbenzene coming into the preheating oven 4, and the other part of the superheated steam is supplied through the line 26 and mixed with ethylbenzene coming out of the oven 4 and enters the first reactor 7. The steam coming out of the heating oven 18 is kept superheated all the time until it is mixed with ethylbenzene via the line 26.

Having generally described this invention, a further understanding can be obtained by reference to certain specific examples which are provided herein for purposes of illustration only and are not intended to be limiting unless otherwise specified.

EXAMPLE 1

Ethylbenzene (EB) was dehydrogenated at a steam/EB molar ratio of 10 in the presence of a commercial Fe-Cr-K catalyst according to the flowsheet represented in the FIGURE. The reaction conditions for each stage and the results obtained are set forth in Table 1. Analysis of the reaction product coming out of the final reactor showed that the conversion of ethylbenzene, selectivity for styrene and yield of styrene were 77.4 mol %, 92.0 mol % and 71.2 mol %, respectively.

COMPARATIVE EXAMPLE 1

Ethylbenzene was dehydrogenated at a steam/EB molar ratio of 13 in the presence of the same catalyst as used in Example 1 and using two reactors. The reaction conditions for each stage and the results obtained are set forth in Table 1. Analysis of the reaction product showed that the conversion of ethylbenzene, selectivity for styrene and yield of styrene were 69.6 mol %, 93.0 mol % and 65.7 mol %, respectively.

COMPARATIVE EXAMPLE 2

Ethylbenzene was dehydrogenated using three reactors as in Example 1 and in the presence of the same catalyst as used in Example 1, except that the pressure at the inlet of the reactor in the final stage was 1.6 kg/cm$^2$ (abs.). The other reaction conditions for each stage and the results obtained are set forth in Table 1. The final conversion of ethylbenzene was 70.0 mol %, the selectivity for styrene was as low as 82.9 mol %, and the yield of styrene was only 58 mol %.

EXAMPLES 2 TO 4

Ethylbenzene was dehydrogenated in a manner similar to the procedure of Example 1 except that in each Example, the temperature at the inlet of each reactor was 650° C. and the steam/EB molar ratio was changed to 4, 6 and 8, respectively.

The other reaction conditions and the results obtained are shown in Table 2.

In all the Examples according to this invention, the high conversion of ethylbenzene was achieved.

TABLE 1

|  | Ex. 1 | Comp. Ex. 1 | Comp. Ex. 2 |
|---|---|---|---|
| 1st stage reactor | | | |
| Inlet temperature (°C.) | 645 | 645 | 645 |
| Inlet pressure (atm) | 1.06 | 1.06 | 1.58 |
| LHSV* (hr$^{-1}$) | 1.18 | 1.18 | 1.18 |
| H$_2$O/EB (mol/mol) | 10 | 13 | 10 |
| EB conversion (mol %) | 43.1 | 46.4 | 40.3 |
| SM selectivity (mol %) | 94.6 | 94.2 | 90.7 |
| 2nd stage reactor | | | |
| Inlet temperature (°C.) | 645 | 645 | 645 |
| Inlet pressure (atm) | 0.84 | 0.89 | 1.46 |
| LHSV* (hr$^{-1}$) | 0.64 | 0.64 | 0.64 |
| H$_2$O/EB (mol/mol) | 10 | 13 | 10 |
| EB conversion (mol %) | 65.6 | 69.6 | 59.9 |
| SM selectivity (mol %) | 93.2 | 93.0 | 86.9 |
| 3rd stage reactor | | | |
| Inlet temperature (°C.) | 645 | | 645 |
| Inlet pressure (atm) | 0.69 | | 1.33 |
| LHSV* (hr$^{-1}$) | 0.44 | | 0.44 |
| H$_2$O/EB (mol/mol) | 10 | | 10 |
| EB conversion (mol %) | 77.4 | | 70.0 |
| SM selectivity (mol %) | 92.8 | | 82.9 |
| SM yield (mol %) | 71.8 | 64.7 | 58.0 |

*LHSV is an abbreviation for liquid hourly space velocity and represents the total LHSVs. up to the respective stage.

TABLE 2

|  | 1st stage reactor | | 2nd stage reactor | | 3rd stage reactor | |
|---|---|---|---|---|---|---|
|  | inlet | outlet | inlet | outlet | inlet | outlet |
| Example 2 | | | | | | |
| temperature (°C.) | 650.0 | 563.3 | 650.0 | 602.9 | 650.0 | 623.4 |
| pressure (atm) | 0.87 | 0.85 | 0.85 | 0.74 | 0.74 | 0.61 |
| H$_2$O/EB (mol/mol) | 4.0 | | | | | |
| LHSV (hr$^{-1}$) | 1.18 | 0.64 | | 0.44 | | |
| EB conversion (mol %) | | 34.1 | | 54.0 | | 66.7 |
| SM selectivity (mol %) | | 94.2 | | 91.7 | | 89.8 |
| SM yield (mol %) | | 32.1 | | 49.5 | | 59.9 |
| Example 3 | | | | | | |
| temperature (°C.) | 650.0 | 566.1 | 650.0 | 605.8 | 650.0 | 626.4 |
| pressure (atm) | 0.907 | 0.88 | 0.88 | 0.75 | 0.75 | 0.61 |
| H$_2$O/EB (mol/mol) | 6.0 | | | | | |
| LHSV (hr$^{-1}$) | 1.18 | 0.64 | | 0.44 | | |
| EB conversion (mol %) | | 38.3 | | 59.6 | | 72.1 |
| SM selectivity (mol %) | | 94.5 | | 92.5 | | 90.9 |
| SM yield (mol %) | | 36.2 | | 55.1 | | 65.6 |
| Example 4 | | | | | | |
| temperature (°C.) | 650.0 | 569.8 | 650.0 | 609.0 | 650.0 | 629.5 |
| pressure (atm) | 0.95 | 0.91 | 0.91 | 0.77 | 0.77 | 0.61 |
| H$_2$O/EB (mol/mol) | 8.0 | | | | | |
| LHSV (hr$^{-1}$) | 1.18 | 0.64 | | 0.44 | | |
| EB conversion (mol %) | | 41.8 | | 64.1 | | 76.3 |
| SM selectivity (mol %) | | 94.6 | | 92.8 | | 91.4 |
| SM yield (mol %) | | 39.5 | | 59.5 | | 69.7 |

Note:
Pressures at the inlet of 2nd and 3rd stage reactors indicate those at the outlet of 1st and 2nd stage reactor, respectively, and include ΔP of respective intermediate heat exchangers.

Having now fully described this invention, it will be apparent to one of ordinary skill in the art that many changes and modifications can be made thereto without departing from the spirit or scope of the invention set forth herein.

What is claimed as new and intended to be covered by Letters Patent is:

1. A process for producing styrene by dehydrogenation of ethylbenzene comprising feeding steam and ethylbenzene to three or more dehydrogenation reactors connected in series, an intermediate heat exchanger for heating the reaction mixture through heat exchange with steam being provided between each of said dehydrogenation reactors, said steam being first used as a medium to heat the respective intermediate heat exchangers, and then said seam being mixed with ethylbenzene supplied as the feed to the first of said series of reactors, wherein 3 to 10 mols of steam are mixed with one mol of ethylbenzene and the temperature and pressure at the inlet of the final dehydrogenation reactor are 600°–680° C. and 0.4–0.8 kg/cm$^2$ (abs.), respectively.

2. The process according to claim 1, wherein the temperature and pressure at the inlet of the dehydrogenation reactors, other than the final reactor, are 600°–680° C. and 2–0.4 kg/cm$^2$ (abs.), respectively.

3. The process according to claim 1, wherein 3 to 8 mols of steam are mixed with one mol of ethylbenzene.

4. The process according to claim 1, wherein the pressure at the inlet of the final dehydrogenation reactor is less than 0.7 kg/cm$^2$ (abs.).

* * * * *

UNITED STATES PATENT AND TRADEMARK OFFICE
CERTIFICATE OF CORRECTION

PATENT NO. : 4,347,396
DATED : August 31, 1982
INVENTOR(S) : HIROTAKA TOKANO ET AL It is certified that error appears in the above—identified patent and that said Letters Patent is hereby corrected as shown below:

On page 1, please delete the name of one of the inventors, namely "HIROTAKA TAKANO" and insert therefor --HIROTAKA TOKANO--.

Signed and Sealed this

Twenty-third Day of November 1982

[SEAL]

Attest:

GERALD J. MOSSINGHOFF

Attesting Officer    Commissioner of Patents and Trademarks